United States Patent [19]

Schleppinghoff et al.

[11] Patent Number: 4,960,961

[45] Date of Patent: Oct. 2, 1990

[54] PROCESS FOR THE PREPARATION OF TERT.-AMYL ALCOHOL (TAA)

[75] Inventors: Bernhard Schleppinghoff, Dormagen; Reiner Malessa, Tübingen; Christian Gabel; Hans-Volker Scheef, both of Dormagen; Mathias Lux, Cologne, all of Fed. Rep. of Germany

[73] Assignee: EC Erdolchemie GmbH, Cologne-Worringen, Fed. Rep. of Germany

[21] Appl. No.: 294,438

[22] Filed: Jan. 6, 1989

[30] Foreign Application Priority Data

Jan. 19, 1988 [DE] Fed. Rep. of Germany ....... 3801273

[51] Int. Cl.$^5$ ..................... C07C 29/04; C07C 31/125
[52] U.S. Cl. ..................................................... 568/899
[58] Field of Search ......................................... 568/899

[56] References Cited

U.S. PATENT DOCUMENTS

| | | | |
|---|---|---|---|
| 2,477,380 | 7/1949 | Kreps et al. | 568/899 |
| 3,257,469 | 6/1966 | Kovsch | 568/899 |
| 4,182,920 | 1/1980 | Giles et al. | 568/899 |
| 4,284,831 | 8/1981 | Okumura et al. | 568/899 |
| 4,327,231 | 4/1982 | Okumura et al. | 568/899 |
| 4,760,202 | 7/1988 | Dettmer et al. | 568/899 |

*Primary Examiner*—J. E. Evans
*Attorney, Agent, or Firm*—Sprung, Horn Kramer & Woods

[57] ABSTRACT

Tert.-Amyl alcohol (TAA) can be prepared in an advantageous manner by hydrating of i-amylenes on an acid cation exchanger by carrying out the reaction in the vicinity of the boiling point of the i-amylenes under the appropriate reaction pressure. A higher content of TAA is thereby obtained in the reaction mixture.

15 Claims, No Drawings

PROCESS FOR THE PREPARATION OF TERT.-AMYL ALCOHOL (TAA)

The invention relates to a process for the preparation of tert.-amyl alcohol (TAA) by hydration of i-amylenes on an acid cation exchanger.

BACKGROUND OF THE INVENTION

U.S. Pat. No. 2,813,908 has already disclosed the hydration of olefines on sulpho-containing styrene/divinylbenzene polymers. U.S. Pat. No. 3,257,469 has disclosed specifically the preparation of TAA on such acid sulpho-containing ion exchangers by the reaction of i-amylene with a molar excess of water. This reaction is carried out, for example, at a pressure of 35 bar and temperatures of 66–107° C. An industrially sufficient proportion of TAA in the reaction product is achieved by additionally using solvents, of which i-propanol and acetone are mentioned in particular. Thus, this process necessarily comprises the removal of the additionally used solvent from the reaction mixture.

U.S. Pat. No. 4,182,920 represents a further development of the process described last and is likewise directed to the preparation of TAA. The fact which is pointed out as novel is that the entire starting mixture forms only one homogeneous phase and a portion of the i-amylene is fed into a second of a total of at least two reactors. The solvent mentioned specifically is acetone, which, according to the working examples, is present in an amount of 60–75% by weight of the total feed stream. This process is likewise carried out using excess molar amounts of water of hydration.

Furthermore, it is a generally known that the hydration of i-butene results in high amounts of tert.-butanol in the reaction mixture, whereas on conversion of i-amylenes substantially lower amounts of TAA are formed in the reaction mixture due to the unfavourable position of equilibrium.

SUMMARY OF THE INVENTION

Surprisingly, it has now been found that substantially higher proportions of TAA in the reaction mixture can be obtained by carrying out the hydration in the vicinity of the boiling point of the i-amylenes. The process according to the invention is successful even without the addition of substances extraneous to the reaction, in particularly without the addition of solvents.

Consequently, the invention relates to a process for the preparation of tert.-amyl alcohols (TAA) by hydration of i-amylenes on an acid cation exchanger, which process is characterized in that it is carried out in the vicinity of the boiling point of the i-amylenes under the set reaction pressure.

DETAILED DESCRIPTION OF THE INVENTION

The process according to the invention is particularly characterized in that it is carried out in the vicinity of the boiling point of the i-amylanes. For this purpose, the reaction is carried out, in particular, in a range from 5° below to 5° above the boiling point of the i-amylenes at the reaction pressures set in each case. Preferably, it is carried out in a range from 5° below to 2° above the boiling point of the i-amylenes, particularly preferably in a range from 2° below to 2° above the boiling point. The adjustment of the boiling point of the i-amylenes as a function of the pressure is known to the person skilled in the art. According to the invention, it is thus possible to shift the boiling point of the i-amylenes to the range of 20–80° C., preferably 35–50° C. A very particularly preferred process variation consists in operating under atmospheric pressure because of the attendant simplification of the apparatuses required.

The acid cation exchangers can be all known types such as sulphonated phenol/formaldehyde resins, sulphonated coumarone/indene condensation products, sulphonated polystyrenes, sulphonated styrene/divinylbenzene resins and the like; according to the invention, they are used in their $H^+$ form. Preferably, according lo the invention, sulphonated styrene/divinylbenzene resins having a crosslinking degree (divinylbenzene content) of 2 to 65%, preferably 8–25%, are used. These acid cation exchangers are known to the person skilled in the art and are commercially available under a multitude of names.

The entire starting mixture is introduced to the acid cation exchangers, which are used as hydration catalysts, in an amount which corresponds to a space velocity (LHSV=liquid hourly space velocity) of 0.05–1 of reaction mixture per litre of catalyst and hour, preferably 0.1 to 0.4 $1/1 \times h$.

In the process$s according to the invention, the amount of water is in principle not critical; thus, even a molar excess of water can be tolerated. The lower limit of the amount of water is generally set to such a value that essentially all i-amylenes are converted to TAA, as long as allowed by the position of the equilibrium of the reaction. If the amount remains under this minimum, the result is unnecessary reduced yields, which are even more undesired since the position of the equilibrium prevents complete conversion of the i-amylenes in the first place. Preferably, 80–120%, particularly preferably 90–115%, very particularly preferably 95 to 105%, of the water amount is therefore used, which leads to the theoretically possible hydration as determined by the position of the equilibrium. The position of the equilibrium is dependent on the reaction temperature chosen, thus making it necessary to adjust the per cent amounts of water to this position of the equilibrium. The variability of the equilibrium as a function of the reaction temperature is known to the person skilled in the art, thus enabling him to determine the percentage range of the amount of water to be chosen by preliminary tests. For increasing the space-time yield, it can also be favourable to set the residence times to values insufficient for reaching the equilibrium. In this case, the amount of water required is calculated for the conversion of i-amylenes obtainable. In the case that the reaction is carried out in two or more reactors instead of in one, it can be advantageous to add only a portion of the entire reaction water (80-120%, relative to the equilibrium expected by theory), for example 60 to 90 per cent, relative to the above per cent range, to the first reactor, while the remaining portions are added to the second or third reactor.

The i-amylenes to be hydrated (2-methyl-1-butene and 2-methyl-2-butene) can be used, for example, in the form of the $C_5$ distillation cut (so-called benzene forerun) or particularly preferably in the form of concentrated or even essentially pure i-amylenes, for example, from the cleavage of tert.-amyl methyl ether.

The process according to the invention allows higher TAA contents in the reaction mixture than processes of the prior art. These higher contents are 25–60% by weight, typically 40–50% by weight, relative to the sum of TAA and i-amylenes (if used as pure i-amylenes, relative to the entire reaction product). Surprisingly, in the process according to the invention, substantially lower contents of $C_5$ dimers are observed than in processes of the prior art. Typical contents of these dimers are 0.01-2%, compared with 5-9% by weight in processes of the prior art.

However, it has been found that the content of dimers can be reduced even further if 0.2-5% by weight, preferably 0.3-4% by weight, particularly preferably 1-3% by weight, of TAA is added to the mixture used, all these amounts being based on the weight of the i-amylene to be hydrated. It is very surprising that the presence of TAA in the reaction mixture, which is the essential feature of the process, is not sufficient still further to suppress the formation of the oligomers and thus the necessity of removing them, and that instead it is necessary that TAA be present in the reaction mixture in the small amount mentioned even before it is added to the hydration catalyst. In principle, the TAA to be added can be added in pure form. However, since the reaction mixture, after leaving the reactor, contains this TAA to be added as the desired reaction product, it is an advantageous variation to add to the starting mixture such an amount of the reaction mixture formed in the process that the desired amount of TAA is present before the start of the catalytic hydration.

The working examples describe working variations without limiting the invention thereto; the person skilled in the art is familiar with a multitude of process modifications.

EXAMPLE 1 (cf. Table)

tert.-Amyl alcohol (TAA) was prepared by reaction of i-amylenes and $H_2O$ at 37° C. and atmospheric pressure in a continuously operating tubular reactor using a styrene/divinylbenzene resin containing acid sulpho groups (commercial product SPC 118 from Bayer AG). The apparatus consisted of a jacket-heated column, in which the cation exchanger was arranged in the form of a solid. A condenser was mounted on the column head to prevent the i-amylenes from escaping. Openings for feeding in water and the i-amylenes were also present at the column head. The feed mixture trickled through the cation exchanger and part of it evaporated. At the bottom of the column, a receiver for the converted reaction mixture was present. At a LHSV of 0.4, a reaction mixture containing 24% of TAA was obtained.

EXAMPLE 2 (cf. Table)

Example 1 was repeated, except that the LHSV was lowered from 0.4 to 0.1 (cf. Table). The TAA content in the reaction mixture was thereby increased to 51%.

TABLE

Synthesis of TAA under atmospheric pressure

|  | Example 1 | Example 2 |
| --- | --- | --- |
| LHSV ($h^{-1}$) | 0.4 | 0.1 |
| Temp. (°C.) | 37° C. | 37° C. |
| Molar ratio of $H_2O$/i-amylenes used | 1:4.9 | 1:2.2 |
| TAA in the product (% by weight) | 24% | 51% |

EXAMPLES 3-5

The apparatus consisted of a glass tube with built-in thimble holder for a Soxhlet thimble for receiving the cation exchanger, a column head adjustable to infinite reflux, and a reboiler with forced circulation at the bottom of the column; the forced circulation recycled the water phase as the heaviest phase located at the bottom of the system. Above the aqueous phase, an organic phase was present, from which TAA was removed. Between Soxhlet thimble and column head, the i-amylenes were fed in, which together with the condensate from the column head trickled through the cation exchanger in the thimble. From the bottom, the i-amylenes, water and TAA were evaporated as an azeotrope. i-Amylenes having a purity of >99% (by gas chromatography) were used.

EXAMPLE 3

As in Example 1, 100 ml of cation exchanger SPC 118 were poured into the Soxhlet thimble.

The following were initially introduced into the bottom of the column:
140.0 g of i-amylene
72.0 g of water (molar ratio 1.0:2.0).

An aqueous and an organic phase were formed.

The bottom circulation was turned on, and the mixture was heated. The entire distillate was recycled through the catalyst bed into the bottom via the infinite reflux.

After three hours, the apparatus was operated continuously.

| Feed: |  |
| --- | --- |
| 30.0 ml/h of i-amylene into the reflux |  |
| 5.0 ml/h of water into the aqueous phase of the bottom |  |
| Molar ratio water/i-amylene 0.97 |  |
| Material removed from the bottom: |  |
| 32.0 ml/h of reaction product from the organic phase |  |
| 3.0 ml/h of water from the aqueous phase |  |
| Temperature of the bottom | 40.0° C. |
| Temperature of the head | 37.0° C. |
| Column pressure | 1.0 bar |
| Reflux ratio (R/E) | infinite |
| LHSV (liquid hourly space velocity) | 0.35 |
| Duration of experiment | 236.0 hours |

| Distribution of products (Example 3): | | | | |
| --- | --- | --- | --- | --- |
| | | | Location | |
| | | Feed | Head | Bottom | Sum |
| Component | | | | | |
| i-amylene | (g/h) | 20.0 | 20.0 | | 20.0 |
| water | (g/h) | 5.0 | | 5.0 | 5.0 |
| total | (g/h) | 25.0 | | | 25.0 |
| | | Discharge | | | |
| Component | | | | | |
| i-amylene | (g/h) | 10.4 | | 10.4 | 10.4 |
| TAA | (g/h) | 11.6 | | 11.6 | 11.6 |
| higher hydrocarbons | (g/h) | 0.05 | | 0.05 | 0.05 |
| hydrocarbon residue | (g/h) | 0.3 | | 0.3 | 0.3 |
| water | (g/h) | 2.65 | | 2.65 | 2.65 |
| total | (g/h) | 25.0 | | | 25.00 |

Yield of TAA: = 11.6 g (0.13 mol) = 46.1%
Conversion of i-amylene: 20.0 − 10.4 = 9.6 g = 48.0%

EXAMPLE 4

The experiment was carried out analogously to Example 3.

The amount of water was minimized according to the conversion and no water was removed.

The continuously running apparatus was reset to the following values:

| Feed: | |
|---|---|
| 30.0 ml/h of i-amylene into the reflux | |
| 2.0 ml/h of water into the aqueous phase of the bottom | |
| Material removed from the bottom: | |
| 32.0 ml/h of reaction product from the organic phase: | |
| Bottom temperature | 40.0° C. |
| Head temperature | 37.0° C. |
| Column pressure | 1.0 bar |
| Reflux ratio (R/E) | infinite |
| LHSV (liquid hourly space velocity) | 0.32 |
| Duration of experiment | 90.0 hours |

Distribution of products (Example 4):

| Component | | Feed | Head | Bottom | Sum |
|---|---|---|---|---|---|
| i-amylene | (g/h) | 20.0 | 20.0 | | 20.0 |
| water | (g/h) | 2.0 | | 2.0 | 2.0 |
| total | (g/h) | 22.0 | | | 22.0 |
| | | Discharge | | | |
| Component | | | | | |
| i-amylene | (g/h) | 10.2 | | 10.2 | 10.2 |
| TAA | (g/h) | 11.5 | | 11.5 | 11.5 |
| higher hydrocarbons | (g/h) | 0.03 | | 0.03 | 0.03 |
| hydrocarbon residue | (g/h) | 0.27 | | 0.27 | 0.27 |
| total | (g/h) | 22.0 | | | 22.00 |

Yield of TAA: = 11.5 g (0.13 mol) = 46.0%
Conversion of i-amylene: 20.0 − 10.2 = 9.8 g = 49.0%

EXAMPLE 5

The experiment was carried out analogously to Example 3.

The i-amylene and water throughput were increased to obtain a higher LHSV.

The continuously running apparatus was reset to the following values:

| Feed: | |
|---|---|
| 50.0 ml/h of i-amylene into the reflux | |
| 8.0 ml/h of water into the aqueous phase of the bottom | |
| Material removed from the bottom: | |
| 53.0 ml/h of reaction product from the organic phase | |
| 5.5 ml/h of water from the aqueous phase | |
| Bottom temperature | 40° C. |
| Head temperature | 37° C. |
| Column pressure | 1.0 bar |
| Reflux ratio (R/E) | infinite |
| LHSV (liquid hourly space velocity) | 0.60 |
| Duration of experiment | 220.0 hours |

Distribution of products (Example 5):

| Component | | Feed | Head | Bottom | Sum |
|---|---|---|---|---|---|
| i-amylene | (g/h) | 33.0 | 33.0 | | 33.0 |
| water | (g/h) | 8.0 | | 8.0 | 8.0 |
| total | (g/h) | 41.0 | | | 41.0 |
| | | Discharge | | | |

Distribution of products (Example 5):

| Component | | Feed | Head | Bottom | Sum |
|---|---|---|---|---|---|
| i-amylene | (g/h) | | | 22.8 | 22.8 |
| TAA | (g/h) | | | 12.5 | 12.5 |
| higher hydrocarbons | (g/h) | <0.01 | | <0.01 | <0.01 |
| hydrocarbon residue | (g/h) | 0.2 | | 0.2 | 0.2 |
| water | (g/h) | | | 5.5 | 5.5 |
| total | (g/h) | 41.0 | | | 41.00 |

Yield of TAA: = 12.5 g (0.13 mol) = 30.0%
Conversion of i-amylene: 33.0 − 22.8 = 10.2 g = 30.8%

We claim:

1. A process for the preparation of tert.-amyl alcohol (TAA) comprising conducting a hydration reaction of a reaction mixture consisting of an (a) i-amylene or a $C_5$-distillation cut containing i-amylene, or a concentrated or essentially pure i-amylene, (b) water and (c) up to 5 weight % TAA, relative to the amount of i-amylene, on an acid cation exchanger, wherein the reaction is carried out in a range from 5° C. below to 5° C. above the boiling point of the i-amylene or the $C_5$-distillation cut.

2. The process according to claim 1, characterized in that the reaction is carried out in a range from 5° C. below to 2° C. above the boiling point of the i-amylenes.

3. The process according to claim 2, characterized in that the reaction is carried out in a range from 2° C. below to 2° C. above the boiling point of the i-amylenes.

4. The process according to claim 1, wherein the boiling point of the i-amylenes varies in the range from 20 to 80° C. depending upon the pressure.

5. The process according to claim 4, characterized in that the boiling point of the i-amylenes varies from 35 to 50° C.

6. The process according to claim 4, wherein the reaction is carried out under atmospheric pressure.

7. The process according to claim 1, characterized in that the space velocity (LHSV=liquid hourly space velocity) is from 0.05 to 1 litre of the starting mixture per litre of catalyst per hour.

8. The process according to claim 1, which further comprises conducting the process in several steps and wherein 60 to 90% of the total water of hydration is added before the first process step and the remaining water is added after the first process step.

9. The process according to claim 1, characterized in that 0.2 to 5% by weight, relative to the weight of the i-amylenes, of TAA is used.

10. The process according to claim 1, characterized in that a sulphonated styrene/divinylbenzene resin is used as the cation exchanger.

11. The process according to claim 10, characterized in that the styrene/divinylbenzene resin has a crosslinking degree (divinylbenzene content) of from 2 to 65%.

12. The process according to claim 11, characterized in that the crosslinking degree is of from 8 to 25%.

13. The process according to claim 9, characterized in that 0.3-4% by weight, relative to the weight of the i-amylenes, of TAA is added to the mixture used.

14. The process according to claim 9, wherein the TAA added to the mixture is in the form of a TAA-containing reaction mixture.

15. A process according to claim 1, wherein the process is conducted in the absence of extraneous solvents.

* * * * *

UNITED STATES PATENT AND TRADEMARK OFFICE
CERTIFICATE OF CORRECTION

PATENT NO. : 4,960,961

DATED : October 2, 1990

INVENTOR(S) : Schleppinghoff et al.

It is certified that error appears in the above-identified patent and that said Letters Patent is hereby corrected as shown below:

Col. 6, line 62    Delete " added to the mixture "

Signed and Sealed this

Twenty-third Day of June, 1992

Attest:

DOUGLAS B. COMER

*Attesting Officer*     Acting Commissioner of Patents and Trademarks